(12) United States Patent
Takehara et al.

(10) Patent No.: US 7,677,857 B2
(45) Date of Patent: Mar. 16, 2010

(54) MOBILE CARGO CONTAINER SCANNING BUFFER CRANE

(75) Inventors: Toru Takehara, San Mateo, CA (US);
Kinya Ichimura, Foster City, CA (US);
Sun Huan Huang, Fremont, CA (US);
Philip Alexander Tam, Emeryville, CA (US)

(73) Assignee: Paceco Corp., Hayward, CA (US)

( * ) Notice: Subject to any disclaimer, the term of this patent is extended or adjusted under 35 U.S.C. 154(b) by 298 days.

(21) Appl. No.: 10/639,957

(22) Filed: Aug. 12, 2003

(65) Prior Publication Data

US 2005/0036854 A1 Feb. 17, 2005

(51) Int. Cl.
*B63B 27/10* (2006.01)
(52) U.S. Cl. .................. 414/140.3; 212/325; 378/57
(58) Field of Classification Search .............. 212/270, 212/271, 324, 325; 378/57; 414/140.3
See application file for complete search history.

(56) References Cited

U.S. PATENT DOCUMENTS

| | | | | |
|---|---|---|---|---|
| 3,247,974 A | * | 4/1966 | Dechantsreiter | 414/591 |
| 3,547,277 A | * | 12/1970 | Strayer | 212/317 |
| 3,812,987 A | * | 5/1974 | Watatani | 414/561 |
| 6,768,421 B1 | * | 7/2004 | Alioto et al. | 340/600 |
| 6,778,631 B2 | * | 8/2004 | Franke | 378/57 |
| 6,845,873 B1 | * | 1/2005 | Chattey | 212/270 |
| 2004/0156477 A1 | * | 8/2004 | Bjorkholm | 378/146 |

FOREIGN PATENT DOCUMENTS

WO 2004/085298 * 1/2004

* cited by examiner

*Primary Examiner*—Thomas J. Brahan
(74) *Attorney, Agent, or Firm*—Brian Beverly; Beeson Skinner Beverly, LLP

(57) ABSTRACT

A mobile cargo container handling buffer crane having a bridge crane mounted thereon for transferring cargo containers between a ship and land transportation with an intermediate transfer position at which a suspended container can be noninvasively inspected by a longitudinally reciprocating container traversing nonintrusive inspection apparatus.

20 Claims, 4 Drawing Sheets

MOBILE CARGO CONTAINER SCANNING BUFFER CRANE

CROSS-REFERENCES TO RELATED APPLICATIONS

The present invention is related to assignees' U.S. Pat. No. 6,604,904 for a Method for Buffer Crane Operation in Cargo Container Handling and to the assignees' U.S. Pat. No. 6,602,036 for Buffer Bridge Crane for Cargo Container Handling Operations, both of which are incorporated herein by reference.

BACKGROUND OF THE INVENTION

1. Field of the Invention

The present invention relates to an apparatus primarily for the purpose of nonintrusive scanning of cargo containers for nuclear based weapons which is intended for use during container transfer between a ship and land transportation.

More particularly it relates to a buffer crane having radiation emission scanning apparatus arranged for nonintrusive interrogation or inspection of cargo containers while each container is being transferred between a ship and quay side land transportation without slowing the quay crane container transfer cycle.

Still more particularly, the present invention is a mobile cargo container buffer and scanning crane which transfers cargo containers between land transportation and a quay crane pickup buffer position and which suspends the cargo container being transferred at a predetermined inspection position for radiation emission examination by a craneboard apparatus before depositing the cargo container at the intended transfer buffer deposition position.

Specifically it relates to a mobile platform having a bridge crane mounted thereon for transferring cargo containers between either a quay crane pickup position, or quay side land transportation, and a predetermined inspection position on said platform where it can be non-intrusively inspected by a longitudinally reciprocating radiation emission inspection apparatus while functioning as a buffer operation. The container is then either deposited on land transportation such as a truck trailer chassis or deposited on the buffer position for pickup by a quay crane for transfer to a ship.

2. Description of the Prior Art

In view of recent terrorist activities throughout the world, considerable effort is being given by analysts to improving security measures with respect to the maritime industry and United States port operations. At the present time, based on the Automated Tracking System, an intelligence based search system used by U.S. Customs, it has been estimated that the probability that contraband will be discovered in containers that are entering the U.S. is less than 50 percent. Thus, the maritime industry provides a delivery system for weapons of mass destruction and every other container could possibly conceal an atomic weapon which, if exploded in a U.S. port, in addition to causing massive destruction, would essentially end international trade.

The methods to be employed to improve U.S. port security may prove severely detrimental to port productivity. The ideal performance standard is 100 percent inspection of inbound containers to U.S. ports. Rather than physically unloading and inspecting the contents of every container, a more efficient alternative is to non-intrusively inspect each container such as by x-ray, and when more sophisticated means of nonintrusive inspection are developed, such as gamma ray scanning and neutron analysis, implementing the use of those developments in addition to x-ray based systems.

The use of x-ray machinery in one manner or another for the purpose of inspecting containers is discussed in the prior art literature. However, implementing prior scanning systems has essentially added processing steps to port operations, and the size of the machinery and complexity of the processing steps have essentially interrupted the established system of port operations. This factor causes problems when attempting to integrate the technology into cargo container handling.

The problem with instituting high-energy x-ray scanners for cargo container examination, apart from safety concerns, is that the equipment will reduce port productivity by disrupting highly developed port operations and consuming valuable terminal space. The primary disadvantage is the interruption of the cargo container transfer process between ship and shore. Most importantly, it interferes with the quay crane offloading cycle time which is crucial to a ship's berthing time at the dock which must be kept at a minimum.

The inspection procedure requires holding a container immobile so that it can be x-rayed. While the cycle times for the x-ray process may ultimately be reduced by improved technology, all of the presently considered means for effecting the x-ray process require either stopping the container movement for processing (usually during unloading in U.S. ports and, if required, during loading at foreign ports) or multiple additional handling steps of the container during the transfer process by taking it out of the normal handling cycle, and to an extra handling step, at an x-ray position for processing, and then returning the container into the transfer cycle.

The present invention permits integration of the x-ray process into the buffer station method of crane operation disclosed in applicant's above-referenced patents such that the inspection process can occur concurrently with the cargo container transfer between ship and shore without interruption of the quay crane transfer cycle.

The mobile cargo container scanning crane contemplated according to the present invention departs substantially from the conventional concepts and designs contemplated by the technical literature, and, in doing so, provides an apparatus primarily developed for the purpose of nonintrusive cargo container inspection during transfer between ship and shore as described above, but it accomplishes the result in a different and improved manner by producing a transfer cycle with a buffer-inclusive procedure for container inspection which is easily integrated into the container transfer cycle for faster processing times and more efficient port operation.

SUMMARY OF THE INVENTION

In view of the foregoing known and obvious disadvantages inherent in the methods of container inspection presently utilized in port operations, the present invention provides a new method, apparatus, and architecture of construction for integrated cargo container inspection during ship and shore container transfers wherein the same can be utilized to maintain port efficiency.

The present invention is a mobile cargo container scanning/buffer crane. It is comprised of a wheel-mounted platform formed for movement in a quay area. The platform has at least a first predetermined container buffer deposition position located thereon for a cargo container where it can be located for pickup or deposition by a quay crane. A bridge crane is mounted above the platform and arranged for engaging and suspending or depositing and releasing a cargo container disposed at the first predetermined position on the platform and moving the container between first and second predetermined positions and between the platform and a truck trailer chassis disposed below or alongside the platform at a third predetermined position. A container scanning inspection apparatus is mounted on the platform and formed to non intrusively inspect a container positioned by the bridge crane at the second predetermined position.

DESCRIPTION OF THE ILLUSTRATED EMBODIMENT

Reference is made to the drawings for a description of the preferred embodiment of the present invention wherein like reference numbers represent like elements in corresponding views.

Figure 1:
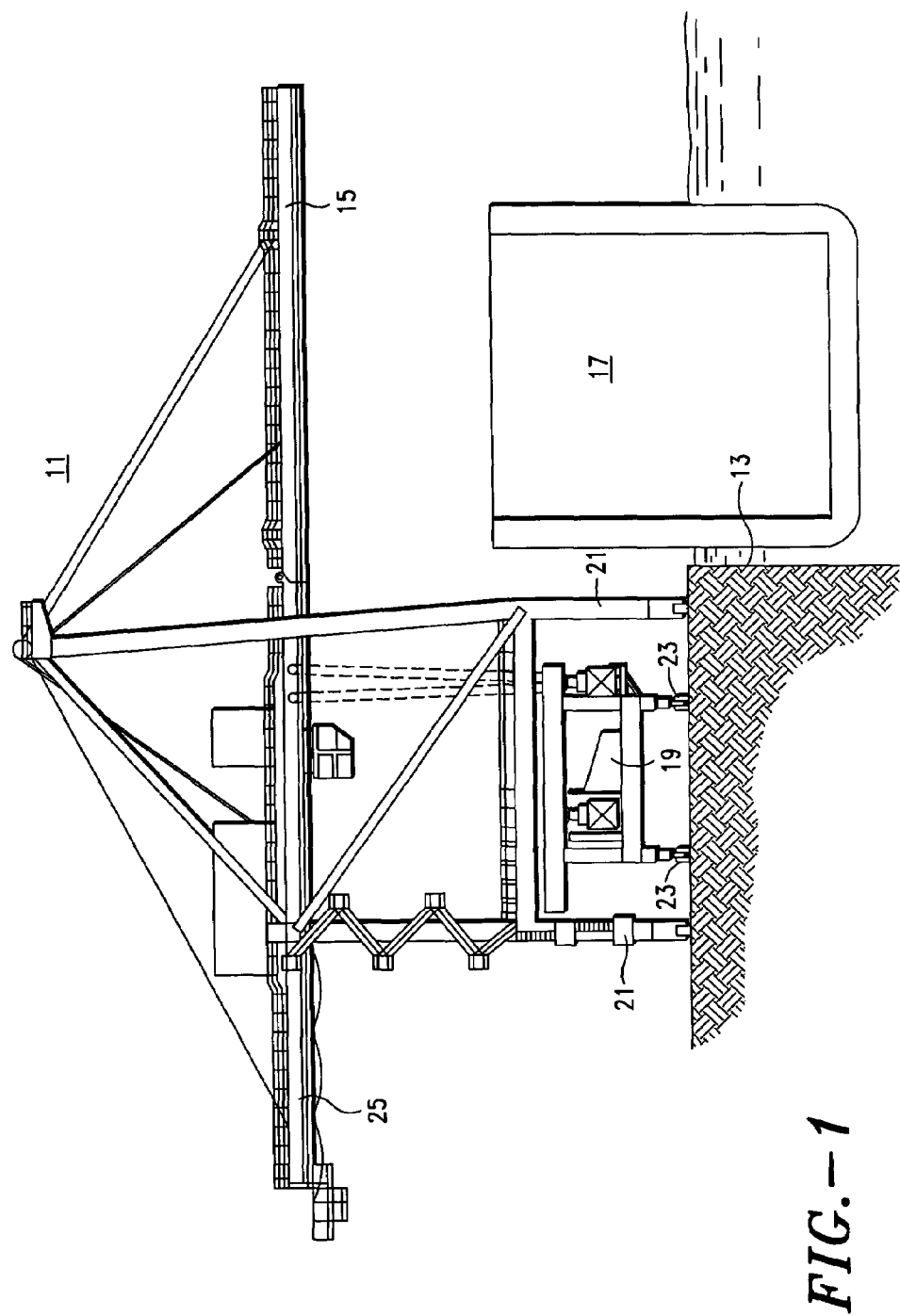
FIG. 1 is a side elevational view of a typical quay crane with a mobile cargo container scanning crane according to the present invention located thereunder.

Reference is made to FIG. 1 of the drawings which shows a typical container handling quay crane 11 located dockside in a shipping port. It is mounted on rails disposed parallel to the dock edge 13. The quay crane traverses the wharf to position itself to project its cantilevered boom 15 over the rows of container cells of the adjacently berthed ship 17 when the boom is lowered. The scanning bridge crane 19 of the present invention is shown disposed below the quay crane between the support legs 21. It comprises a rigid framework having four or more legs mounted on pneumatic tires 23 for independent movement on the wharf such that it can be located at variable positions below or adjacent to the quay crane either between the support legs or alongside under a cantilevered shoreside back reach 25.

The scanning crane 19 is a low-profile buffer crane having a maximum height permitting it to be positioned underneath a quay crane 11 between its support legs 21 during container handling operations. It is contemplated that a buffer/scanning crane could also be utilized in a railroad stacking yard, under a large bridge or straddle crane, as well as dockside, so the term "quay crane" as used in the claims to describe the environment of the invention is intended to include these and other types of container storage yard and railyard container handling cranes as well.

Figure 2:
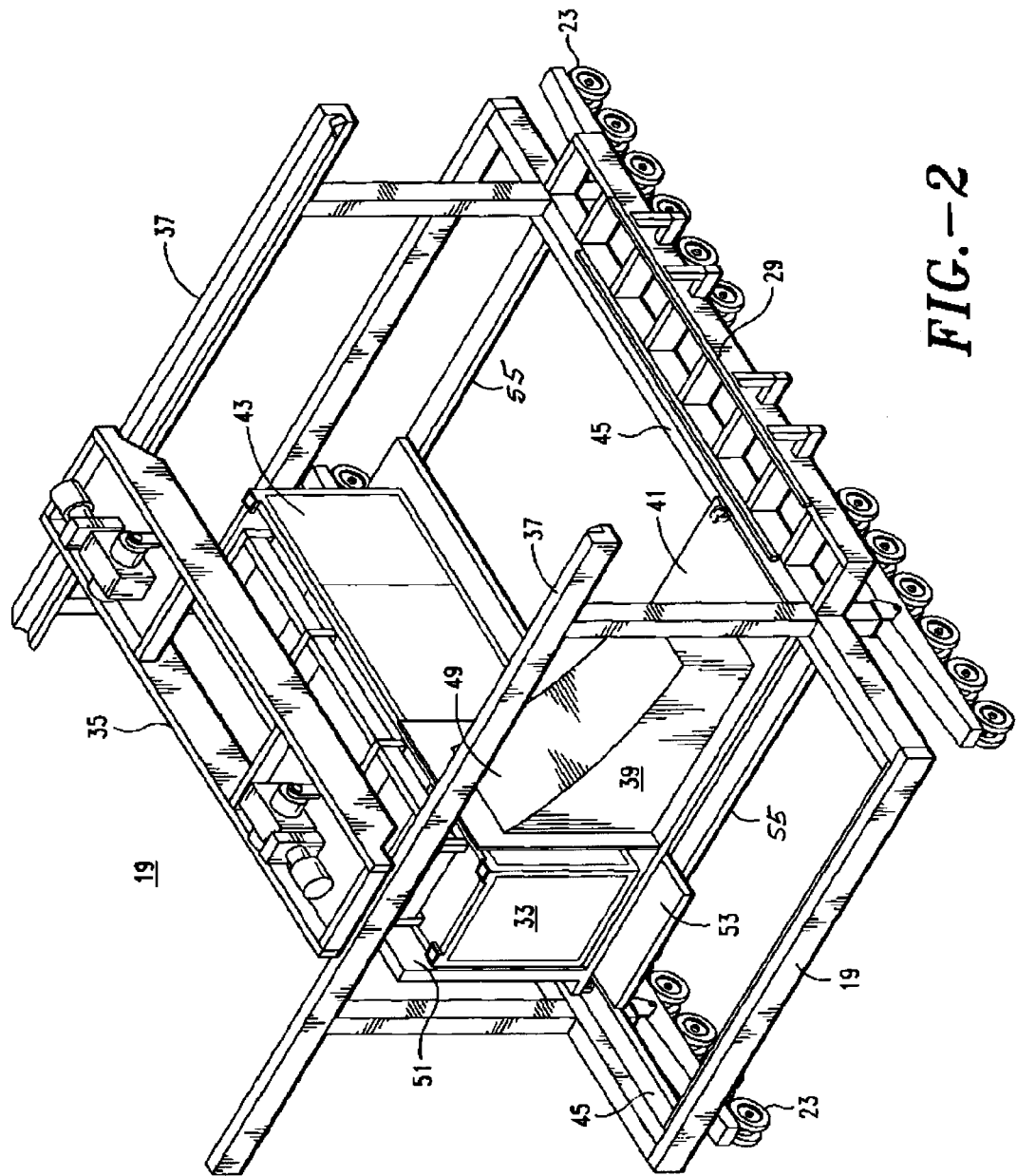
FIG. 2 is an upper perspective view of the scanning crane of the present invention shown in operation.
Figure 3:
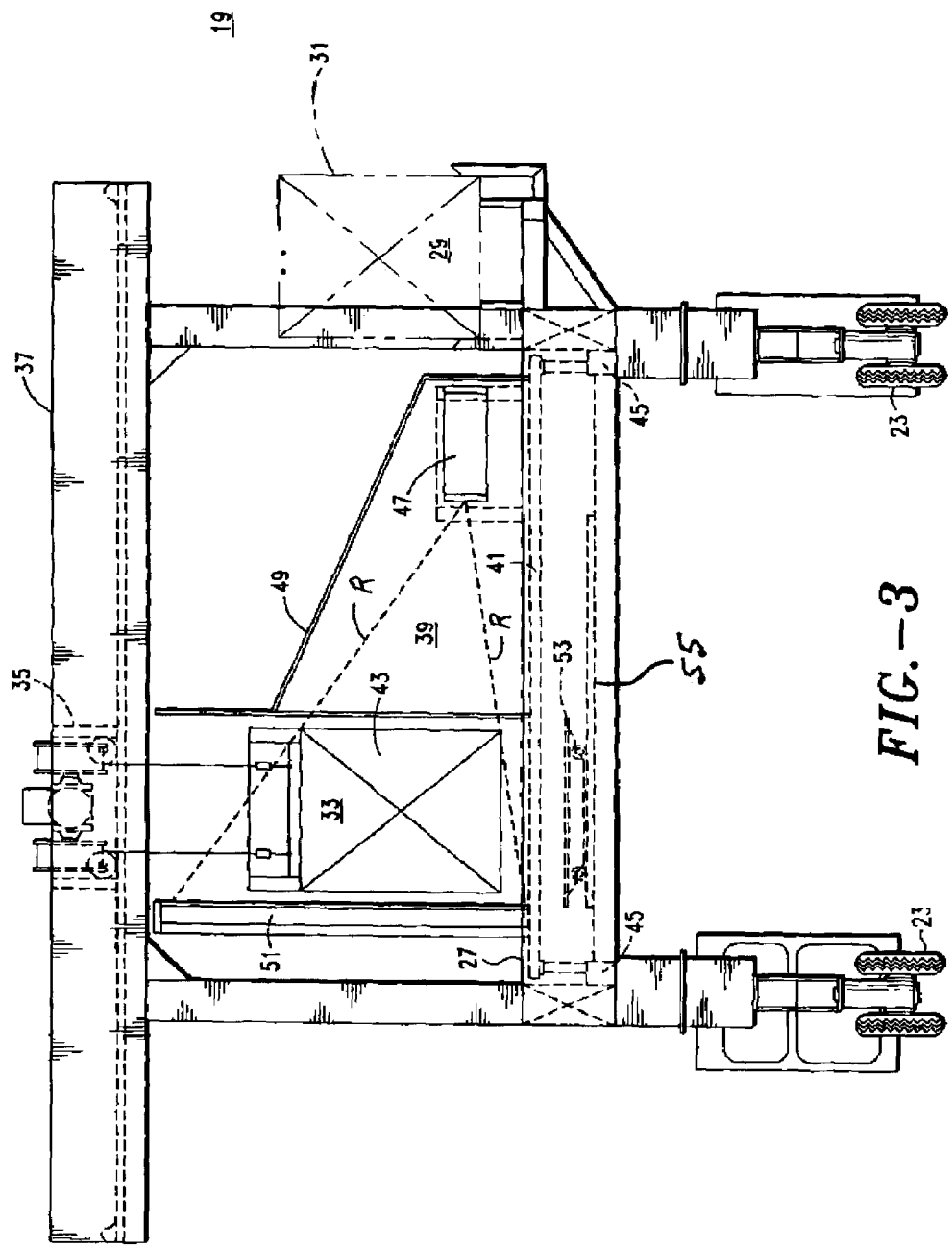
FIG. 3 is an end view of the scanning crane shown in FIG. 2.
Figure 4:
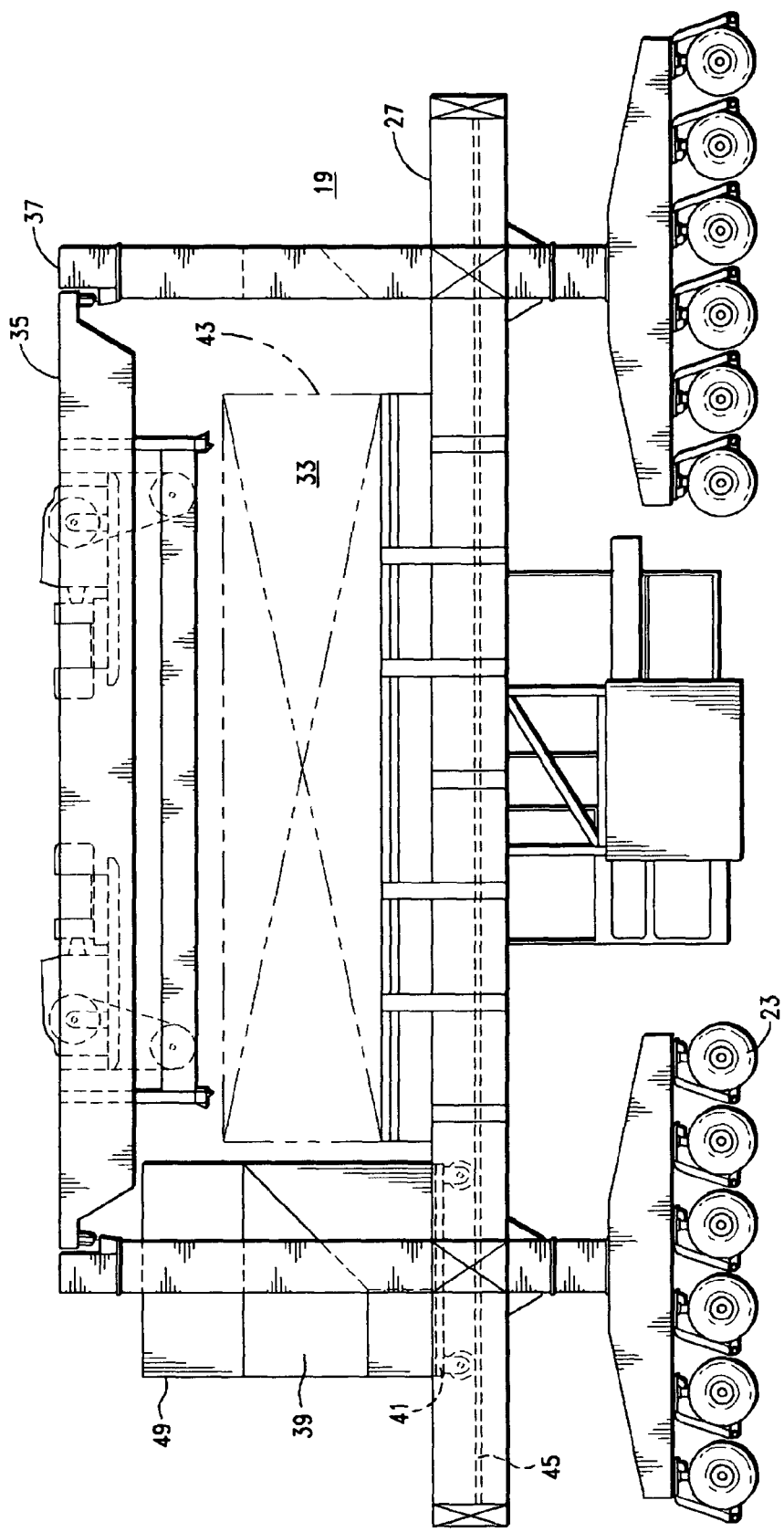
FIG. 4 is a side elevational view of the scanning crane shown in FIG. 2.

Reference is made to FIGS. 2-4 which disclose a mobile cargo container buffer/scanning bridge crane 19 in operation as contemplated by the present invention. The crane is comprised of a multiple tire 23 or a wheel-supported platform 27 having a floor and formed for independent movement in a quay area. It is essentially a landing deck mounted on legs so that container transporters can pass underneath. Containers can be landed on the deck and temporarily stored by a quay crane when they are removed from shipboard or where containers picked off ground level transporters can be landed and stored until they are picked up by the quay crane for transport to a ship. The landing deck can thereby function as a buffer crane quite effectively and even more so when constructed with multiple landing positions for containers as described in the patents described supra and incorporated herein.

The landing deck or platform 27 has a first predetermined position 29 (see FIG. 3) for the deposit of containers 31 which have been offloaded from a ship by a quay crane or where containers being transferred from land transportation can be landed until picked up by the quay crane for transfer to a ship. This first predetermined position is labeled the "first" for designation purposes and does not necessarily describe its position as a sequence step in container transfer operations except in the one specific mode of crane operation: ship to shore transfer. Conversely, it is the last predetermined position in a shore to ship container transfer. Therefore, the designation as a first position is an arbitrary selection simply because the most immediate need in the industry is for inspection of containers being landed in the United States, and that sequence starts with the quay crane landing the container first on the buffer deposition position of the scanning crane.

This first predetermined position 29 can actually be comprised of a number of landing positions for the temporary storage of containers during ship loading and unloading operations whereby the scanning crane 19 can also function as a buffer crane as taught by applicant's related and incorporated patents, although a single buffer deposition position can be sufficient under some conditions for the scanning crane to function adequately as a buffer crane.

The scanning buffer crane 19 has a second predetermined position 33 which, in the illustrated embodiment of the invention, is a suspended position where a container is held for nonintrusive examination. It can also be a landing position depending upon the type of scanning apparatus which is employed.

The scanning crane 19 can remain engaged to or hold onto a container being transferred between ship and shore for a reasonably long period of time during the transfer operations in relation to the cycle time of the quay crane 11 in order to inspect a container.

The quay crane 11 requires time to engage a container, either on board a ship in a container cell, or shoreside from a dockside transporter or a buffer crane, and then to lift the container to shipboard clearance height while translating it horizontally between ship and shore, and then for lowering the container to an accurate deposition height and position for release either into a shipboard cell or onto a predetermined position on a buffer crane or onto a ground transporter. This quay crane transfer cycle requires considerably more time than the scanning crane needs to engage a container, lift and move it a short distance into inspection position, take the necessary time to scan it, and deposit it at the predetermined release position. As a result, the scanning crane, when incorporated into a buffer operation, can perform the scanning operation without interrupting the quay crane cycle times. The related patents, supra, disclose a buffer crane which includes multiple landing/storage positions to ensure that a fully functional buffer operation is achieved, but even a single buffer container landing position on a scanning crane will be sufficient for performing a buffer operation in those cases where the quay crane transfer cycle times are sufficiently slow.

A bridge crane 35 is mounted on a pair of leg-supported crossbeams 37 above the mobile platform and generally spans the length of the cargo containers it is intended to handle. It is arranged for engaging either a cargo container mounted on a truck trailer chassis disposed either below or alongside the platform at the third predetermined position or for depositing a container onto the platform. The bridge crane lifts or lowers the containers between the third and second predetermined positions through an opening in the floor of the landing deck. In those situations where the clearance height under the crossmembers extending between the legs of a quay crane is limited, it may not be possible to drive container transporters under the scanning crane. In that case, it would be necessary to lift or deposit containers from and to transporters parked alongside the scanning crane. To do so, the support rails for the bridge crane on the crossbeams 37 would be extended to project laterally over the adjacent truck parking positions with cantilevered beam projections.

The bridge crane 35 is formed for raising a container from a trailer chassis to the platform height at the second predetermined position which is disposed at one side of the platform. It is also formed for moving horizontally and translating a container to the first predetermined container landing position(s) and depositing it thereon. In other words, the bridge crane moves containers between land transportation (third predetermined position) and the quay crane landing positions (first predetermined position) with an intermediate container hold position (second predetermined position) for container examination during the transfer cycle. The second predetermined position in the preferred embodiment of the invention is a suspended position, usually above the third predetermined position.

A container scanning inspection or interrogation apparatus 39 is mounted on the platform 27 and is formed for reciprocating longitudinal movement on a trolley 41 above the platform 27 to traverse the length of a cargo container 43 suspended by the bridge crane 35 at the second predetermined position 33. It is mounted on a wheeled trolley which runs on rails 45 that extend for substantially the length of the platform. The second predetermined position could be a deposition position on the front of the scanning apparatus support platform.

The scanning apparatus 39 can be provided with a hold or rest position at one end of the platform as shown in FIG. 4 to permit the vertical transfer of containers between the second and third predetermined positions without mechanical interference. Such a hold position for the scanning apparatus may not be necessary. As presently envisioned, due to the physical construction and space requirements of presently available and utilized scanning apparatus, the reciprocating and translating trolley 41 is mounted on a first set of dual parallel tracks 45 so it can slide horizontally from one end of a container 43, suspended at the second predetermined position 33, to the other. In all likelihood, the scanning apparatus 39 will have to be able to traverse the length of a container, but it is possible that with improved scanning techniques, it will only need to move to one or more fixed positions along the length of the container. In such a case, the second predetermined position could be a buffer deposition position on the front of the scanning apparatus trolley platform 41. Nevertheless, with reference to FIGS. 2-4, it can be seen that when the scanning apparatus 39 is in the rest position, as shown in FIG. 4, the first set of tracks 45 are sufficiently spaced apart such that cargo container 43 can be raised and lowered between tracks 45 to and from the second predetermined position 33, shown in FIGS. 2 and 3, and land transportation vehicles at ground level below tracks 45.

With reference now to FIG. 3, the scanning apparatus 39 envisioned by the present invention includes a focused radiation emitter 47 housed in a shield 49 which directs radiation R, shown in dotted lines, toward the container 43 suspended at the second predetermined position 33. A receptive screen and radiation shield 51 are positioned behind the container and supported by the same reciprocating platform or trolley 41 which supports the radiation emitter and its shielding. The scanning apparatus support and trolley platform 41 also functions as a shield to prevent radiation from scattering downward in order to protect dockside workers and truck driver personnel located under the platform 27. A shield door 53 mounted on rollers can be provided under the scanning apparatus to cover the access door in the floor of the landing deck during scanning to prevent radiation from reaching the truck drivers and dock personnel. In the illustrated embodiment, shield door 53 is supported on a second set of dual, spaced-apart tracks 55 disposed perpendicularly to and below the first set of tracks 45. Shield door 53 can thence be rolled from a first position directly below a cargo container 43 being held suspended in the second predetermined position 33, as seen in FIGS. 2 and 3, to a second position horizontally removed from the second predetermined position 33. Thus, when the shield door 53 is moved away from the first position the cargo container 43 can be moved vertically between the second set of tracks 55 to and from the second predetermined position 33 and land transportation vehicles at ground level.

When a cargo container is transferred by the bridge crane from either the landside transportation (third predetermined position) or the quay crane landing position (first predetermined position) 29 to the intended receiving deposition position, it is stopped during transit at the second predetermined position 33, and the nonintrusive scanning apparatus 39 moves along the length of the landing platform 27 to scan the suspended container 43 at the second predetermined position before it is lowered onto the land transportation truck trailer chassis or moved to land on one of the buffer crane landing positions (the first predetermined position) 29.

The presently available scanning apparatus 39 can include x-ray machines and gamma ray detectors, and eventually neutron analysis machines. These latter devices may not require the capability of moving along the container to scan it. Positioning it at one place in relation to the scanning apparatus may be sufficient and permit the container to be deposited on the landing deck at a buffer position while the scanning apparatus performs its function. The term scanning apparatus is intended to include all forms of radiation emissions generation and detection equipment used in the present invention. When new and improved noninvasive scanning equipment evolves, it can be substituted for the radiation emission generation or detection equipment then mounted on the translating platform. Modifications to the present apparatus are envisioned as coming within the concept and apparatus of the present invention as claimed.

The present invention provides a container scanning crane which can function as a buffer between two port operations and allows the other port operations to continue uninterrupted. Security scanning or screening occurs while a container is located in a buffer whereby the port operations continue to function without interruption. The scanning crane provides its own bridge crane for independent handling of the containers and includes a reciprocating trolley that is capable of moving the scanning apparatus along the length of a container which has been picked up by the bridge crane. The invention positions the scanning apparatus above the dockside truck operations so that it does not interfere with the flow of trucks on the wharf. The scanning crane is an independent machine which can be installed in ports with minimum modifications to the facilities.

While a mobile cargo container scanning buffer crane is illustrated and described in considerable detail herein, the invention is not to be limited to such details, the spirit and scope of the present invention being limited only by the terms of the appended claims and their legal equivalents.

We claim:

1. A mobile cargo container scanning buffer crane comprising:
    a platform mounted on tires formed for independent movement of said platform on the wharf in a quay area whereby it can be located at variable positions below or adjacent to a container handling quay crane, said platform having at least a first predetermined container deposition buffer position and dual parallel horizontal tracks, said first predetermined container deposition buffer position located thereon disposed on the dock edge side of said platform where a cargo container can be located for pickup or deposition by a quay crane, a bridge crane mounted above said platform and arranged for engaging and suspending or depositing and releasing a cargo container at said first predetermined position on said platform, said bridge crane also arranged for moving a container between said first predetermined position and a second predetermined position disposed at or above platform height, and a container scanning inspection apparatus mounted on said tracks and formed to nonintrusively inspect a container positioned by said bridge crane at said second predetermined position, said bridge crane further arranged for moving a container vertically between said tracks to and from said second predetermined position and a truck trailer chassis located below or alongside said platform at a third predetermined position.

2. The mobile cargo container scanning crane of claim 1 wherein:

said scanning apparatus is formed for reciprocating longitudinal movement on said platform parallel to the longitudinal dimension of a container disposed in said second predetermined position to traverse the length of said container.

3. The mobile cargo container scanning crane of claim 1 wherein:

said first predetermined container deposition buffer position includes a multiple thereof to permit said scanning crane to function as a buffer crane.

4. The mobile cargo container scanning crane of claim 1 wherein:

said second predetermined position is a suspended position.

5. A mobile cargo container scanning crane comprising:

a platform mounted on tires formed for independent movement of said platform on the wharf in a quay area whereby it can be located at variable positions below or adjacent to a container handling quay crane, said platform having at least a first predetermined container deposition buffer position and dual parallel horizontal tracks, said first predetermined container deposition buffer position located thereon disposed on the dock edge side of said platform where a cargo container can be located for pickup or deposition by a quay crane, a bridge crane mounted above said platform and arranged for engaging and suspending or depositing and releasing a cargo container at said first predetermined position on said platform, said bridge crane also arranged for moving a container between said first predetermined position and a second predetermined position disposed at or above platform height, a container scanning inspection apparatus mounted on said tracks and formed to nonintrusively inspect a container positioned by said bridge crane at said second predetermined position, said bridge crane further arranged for moving a container vertically between said tracks to and from said second predetermined position and a truck trailer chassis located below or alongside said platform at a third predetermined position, and a floor having an opening above said third predetermined container landing position through which containers are moved vertically between said second and third predetermined positions, and a sliding horizontal shield to cover said opening when said scanning apparatus is operating.

6. A mobile cargo container scanning buffer crane comprising:

a platform mounted on tires formed for independent movement of said platform on the wharf in a quay area whereby it can be located at variable positions below or adjacent to a container handling quay crane, said platform having a multiple of first predetermined container deposition buffer positions located thereon where one or more cargo containers can be located for pickup or deposition by a quay crane, a bridge crane mounted above said platform and arranged for engaging and suspending or depositing and releasing a cargo container at one of said first predetermined positions on said platform, said bridge crane also arranged for moving a container between said first predetermined positions and a second predetermined position disposed at platform height, said bridge crane further arranged for moving a container between said second predetermined position and a truck trailer chassis located below or alongside said platform at a third predetermined position, said platform having a floor including an opening above said third predetermined container landing position through which containers are lifted and lowered from and to said third predetermined position to and from said second predetermined position, a container scanning inspection apparatus mounted on said platform and formed for reciprocating longitudinal movement on said platform to traverse the length of a container positioned by said bridge crane at said second predetermined position to nonintrusively inspect a container positioned by said bridge crane at said second predetermined position, and a sliding horizontal shield to cover said opening when said scanning apparatus is operating.

7. A mobile cargo container scanning buffer crane for use in cooperation with a ship-to-shore quay crane, the mobile cargo container scanning buffer crane comprising:

a rigid framework having a landing deck, a bridge crane, and a first set of dual parallel horizontal tracks, said landing deck arranged for deposition of one or more cargo containers thereon by a quay crane, said bridge crane capable of moving a cargo container between said landing deck and a suspended position above said first set of tracks, and a cargo container scanning apparatus movable on said first set of tracks to a rest position horizontally spaced from said suspended position, said scanning apparatus movable on said first set of tracks along the length of a cargo container disposed in said suspended position for scanning the contents of the container, said first set of tracks spaced apart sufficiently such that when said scanning apparatus is disposed in said rest position a cargo container can be moved between said first set of tracks by said bridge crane to and from said suspended position and a lower position below said first set of tracks at the level of a land transportation vehicle.

8. The mobile cargo container scanning crane of claim 7 wherein:

said bridge crane is movable horizontally in a direction perpendicular to said first set of tracks.

9. The mobile cargo container scanning crane of claim 7 further comprising:

said framework having four legs, and one or more tires supporting each of said legs such that said framework is capable of being rolled independently to a selected location.

10. The mobile cargo container scanning crane of claim 7 wherein:

said framework has a maximum height lower than the crossmembers extending between the support legs of the quay crane such that said framework can be moved underneath the quay crane.

11. The mobile cargo container scanning crane of claim 7 wherein:

said first set of tracks are disposed at a height sufficient for a ground-based container transporter loaded with at least one container to pass thereunder.

12. The mobile cargo container scanning crane of claim 7 wherein:

said scanning apparatus includes a wheeled trolley, and a focused radiation emitter, a shield, and a receptive screen mounted on said trolley, said trolley being movable on said first set of tracks beneath a cargo container disposed in said suspended position, said shield disposed on one side of the container for directing radiation from said radiation emitter toward the container, and said receptive screen positioned on the opposite side of the container for intercepting said radiation.

13. The mobile cargo container scanning crane of claim 12 wherein:

said trolley is for intercepting said radiation to prevent it from scattering downward.

14. The mobile cargo container scanning crane of claim 7 further comprising:

a second set of dual parallel horizontal tracks, a secondary radiation shield movable on said second set of tracks between a first position disposed directly below a cargo container held in said suspended position and a second position horizontally spaced said first position, said secondary shield for intercepting radiation from said radiation emitter to prevent it from scattering downward, said second set of tracks spaced apart sufficiently such that when said shield is disposed in said second position, a cargo container may be moved vertically between said second set of tracks by said bridge crane to and from said suspended position and said lower position.

15. The mobile cargo container scanning crane of claim 14 wherein:

said second set of dual parallel horizontal tracks is disposed perpendicularly to said first set of dual parallel horizontal tracks.

16. The mobile cargo container scanning crane of claim 14 wherein:

said second set of tracks is disposed below said first set of tracks.

17. The mobile cargo container scanning crane of claim 14 wherein:

said second set of tracks is disposed at a height sufficient for a ground-based container transporter loaded with at least one cargo container to pass thereunder.

18. The mobile cargo container scanning crane of claim 14 wherein:

said secondary shield has rollers supported on said second set of tracks.

19. A mobile cargo container scanning buffer crane for use in cooperation with a ship-to-shore quay crane, the mobile cargo container scanning buffer crane comprising:

a rigid framework having a landing deck, a bridge crane, a first set of dual parallel horizontal tracks, four legs, and one or more tires supporting each of said legs such that said framework is capable of being rolled independently to a selected location, said landing deck arranged for deposition thereon of one or more cargo containers by the quay crane, said bridge crane capable of moving a cargo container between said landing deck and a suspended position above said first set of tracks, a cargo container scanning apparatus including a wheeled trolley, and a focused radiation emitter, a primary shield, and a receptive screen all mounted on said trolley, said trolley movable on said first set of tracks beneath a cargo container disposed in said suspended position for moving said radiation emitter, said primary shield and said receptive screen along the length of the cargo container for scanning the contents of the container, said primary shield disposed on one side of the container for directing radiation from said radiation emitter toward the container, said receptive screen positioned on the other side of the container for intercepting said radiation, and said scanning apparatus movable on said first set of tracks to a rest position horizontally spaced from said suspended position, said first set of tracks spaced apart sufficiently such that when said scanning apparatus is disposed in said rest position a cargo container can be moved between said first set of tracks by said bridge crane to and from said suspended position and a lower position below said first set of tracks at the level of a land transportation vehicle.

20. A mobile cargo container scanning buffer crane for use in cooperation with a ship-to-shore quay crane, the mobile cargo container scanning buffer crane comprising:

a rigid framework having a landing deck, a bridge crane, a first set of dual parallel horizontal tracks, four legs, and one or more tires supporting each of said legs such that said framework is capable of being rolled independently to a selected location, said framework having a maximum height lower than the crossmembers extending between the support legs of the quay crane such that said framework can be moved underneath the quay crane, said landing deck arranged for deposition thereon of one or more cargo containers by the quay crane, said bridge crane capable of moving a cargo container between said landing deck and a suspended position above and horizontally spaced from said landing deck in a direction perpendicular to said first set of tracks, and a cargo container scanning apparatus including a wheeled trolley, and a focused radiation emitter, a primary shield, and a receptive screen all mounted on said trolley, said trolley movable on said first set of tracks beneath a cargo container disposed in said suspended position for moving said radiation emitter, said primary shield and said receptive screen along the length of the cargo container for scanning the contents of the container, said primary shield disposed on one side of the container for directing radiation from said radiation emitter toward the container, said receptive screen positioned on the other side of the container for intercepting said radiation, and said scanning apparatus movable on said first set of tracks to a rest position horizontally spaced from said suspended position, said first set of tracks spaced apart sufficiently such that when said scanning apparatus is disposed in said rest position a cargo container can be moved between said first set of tracks by said bridge crane to and from said suspended position and a lower position below said first set of tracks at the level of a land transportation vehicle, a second set of dual parallel horizontal tracks disposed perpendicularly to said first set of dual parallel horizontal tracks, and a secondary radiation shield movable on said second set of tracks between a first position disposed directly below a cargo container held in said suspended position and a second position horizontally spaced said first position, said secondary shield for intercepting radiation from said radiation emitter to prevent it from scattering downward, said second set of tracks spaced apart sufficiently such that when said shield is in said second position, a cargo container may be moved between said second set of tracks by said bridge crane to and from said suspended position and said lower position.

* * * * *

UNITED STATES PATENT AND TRADEMARK OFFICE
CERTIFICATE OF CORRECTION

PATENT NO. : 7,677,857 B2
APPLICATION NO. : 10/639957
DATED : March 16, 2010
INVENTOR(S) : Toru Takehara et al.

It is certified that error appears in the above-identified patent and that said Letters Patent is hereby corrected as shown below:

In column 4, line 7, "in the one" should read --in one--.
In column 4, line 59, "for engaging either" should read --either for engaging--.
In column 6, line 45, --which-- should be inserted between "and" and "allows".
In column 9, line 44, claim 14, --from-- should be inserted between "spaced" and "said".
In column 12, line 4, claim 20, --from-- should be inserted between "spaced" and "said".

Signed and Sealed this

Twelfth Day of October, 2010

David J. Kappos
*Director of the United States Patent and Trademark Office*